(12) United States Patent
Kim et al.

(10) Patent No.: US 6,359,126 B1
(45) Date of Patent: Mar. 19, 2002

(54) ANTIBODIES TO αVβ3 INTEGRIN

(75) Inventors: Kyung Jin Kim, San Francisco, CA (US); Michael A. Horton, Essex (GB); Sarah C. Bodary, San Francisco; Anan Chuntharapai, Colma, both of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 08/874,837

(22) Filed: Jun. 13, 1997

Related U.S. Application Data

(63) Continuation of application No. 08/432,618, filed on May 2, 1995, now Pat. No. 5,652,110, which is a continuation of application No. 08/307,844, filed as application No. PCT/US93/02987 on Mar. 30, 1993, now Pat. No. 5,578,704, which is a continuation-in-part of application No. 08/025,913, filed on Mar. 3, 1993, now abandoned, which is a continuation of application No. 07/862,679, filed on Apr. 3, 1992, now abandoned.

(51) Int. Cl.$^7$ .................. C07H 21/04; C07K 16/00; C07K 17/00
(52) U.S. Cl. ............... 536/23.53; 536/23.5; 530/324; 530/350; 530/387.1; 530/388.22; 530/388.1; 530/867
(58) Field of Search ................. 536/23.5, 23.53; 530/867, 324, 350, 387.1, 388.1, 388.22

(56) References Cited

U.S. PATENT DOCUMENTS

| 4,707,352 A | 11/1987 | Stavrianopoulos |
| 5,057,604 A | 10/1991 | Brown |

FOREIGN PATENT DOCUMENTS

| WO | 89/05155 | 6/1989 |
| WO | 92/08739 | 5/1992 |

OTHER PUBLICATIONS

Charo et al., "The Vitonectin Receptor $α_3β_3$ Binds Fibronectin and Acts in Concert with $α_5β_1$ in Promoting Cellular Attachment and Spreading on Fibronectin," *The Journal of Cell Biology* (part 1):2795–2800 (1900).

Cheresh et al., "Biosynthetic and Functional Properties of an Arg–Gly–Asp–directed Receptor Involved in Human Melanoma Cell Attachment to Vitronectin, Fibrinogen, and von Willebrand Factor," *Journal of Biological Chemistry*, 262(36):17703–17711 (1987).

Davies et al., "The Osteoclast Functional Antigen, Implicated in the Regulation of Bone Resorption, is Biochemically Related to the Vitronectin Receptor," *The Journal of Cell Biology*, 109;1817–1826 (1989).

Goding, "Fragementation of Monoclonal Antibodies," *Monoclonal Antibodies: Principles and Practice*, Academic Press, Inc.: London, pp. 118–124 (1983).

Goding, "Solid–Phase Radioimmunoassy Soluble Protein Antigen," *Monoclonal Antibodies:Principles and Practice*, Academic Press, Inc.: London, pp. 75–84 (1983).

Helfrich et al., "Integrins on Rat Osteoclasts: Characterization of Two Monoclonal Antibodies (F4 and F11 to Rat $β_3$," *Journal of Bone and Mineral Research*, 7(3):345–351 (1992).

Horton, "Osteoclast–Specific Antigens," *ISI Atlas of Science: Immunology*, pp. 35–43 (1988).

Horton et al., "Arg–Gly–Asp (RGD) Peptides and the Anti–Vitronectin Receptor Antibody 23C6 Inhibit Dentine Resorption and Cell Spreading by Osteoclasts," *Experimental Cell Research* 195:368–375 (1991).

Horton et al., "Monoclonal Antibodies to Osteoclastomas (Giant Cell Bone Tumors): Definition of Osteoclast–Specific Cellular Antigens," *Cancer Research*, 5:5663–5669 (1985).

Horton et al., "Perspectives: Adhesion Receptors in Bone,"0 *Journal of Bone and Mineral Research*, 4(6):803–808 (1989).

Horton, "Current Status Review Vitronectin Receptor: Tissue Specific Expression or Adaptation to Culture?" *Int. J. Exp. Pathol.*, 71:741–759 (1990).

Hynes, "Integrins: A Family of Cell Surface Receptors," *Cell*, 48:549–554 (1987).

Nesbitt et al., "Epitope Analysis of the Vitronectin Receptor (CD51)," *Leukocyte Typeing IV: White Cell Differentiation Antigens*, Knapp et al. (Eds.), p. 1037 (1991).

Nesbitt et al., "Epitope Analysis of the Vitronectin Receptor α and β Chains," *Tissue Antigens* (abstract only), 33:357 (1989).

Ruoslahti et al., "Arg–Gly–Asp: A Versatile Cell Recognition Signal," *Cell*, 44:517–518 (1986).

Ruoslahti et al., "New Perspective in Cell Adhesion: RGD and Integrins," *Science*, 238:491–497 (1987).

Waldmann, "Monoclonal Antibodies in Diagnosis and Therapy," *Science*, 252:1657–1662 (1991).

Roitt, "Essential Immunology" Blackwell Scientific Publications: Oxford, pp. 65–68 and 74 (1991).

Harlow et al., "Antibodies: A Laboratory Manual," Cold Spring Harbor Laboratory: New York, pp. 321–358 and 513–552 (1988).

Vitetta et al., "Redesigning Nature's Poisons to Create Anti–Tumor Reagents," *Science*, 238:1098–1104 (1987).

*Primary Examiner*—Geetha P. Bansal
(74) *Attorney, Agent, or Firm*—Mark T. Kresnak; Flehr Hohbach Test Albritton & Herbert LLP

(57) ABSTRACT

The invention relates to monoclonal antibodies to the αvβ3 integrin receptor known to be expressed in large amounts on the surface of osteoclasts and accordingly, associated with bone resorption. The disclosed monoclonal antibodies recognize unique epitopes on αvβ3 and are useful in the treatment of conditions associated with excessive bone resorption and/or in the inhibition of tumor cell growth.

28 Claims, 8 Drawing Sheets

FIG._1

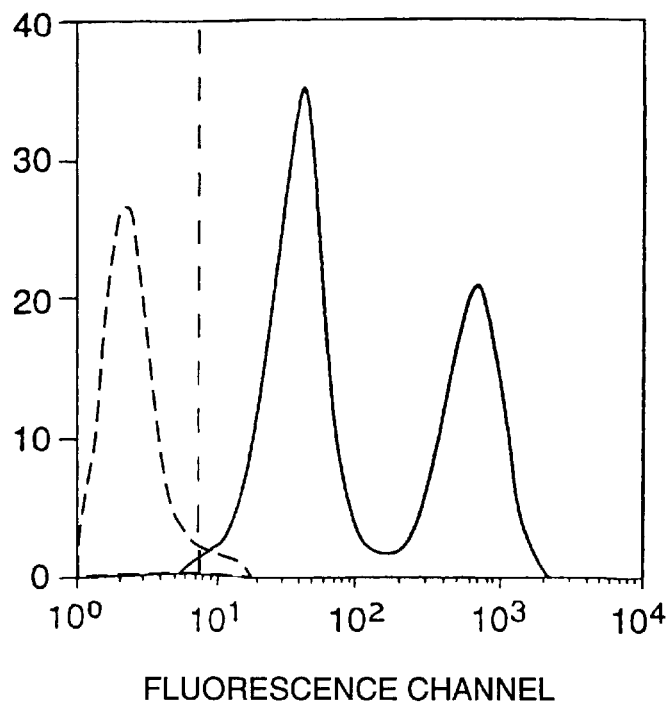
FIG._3A
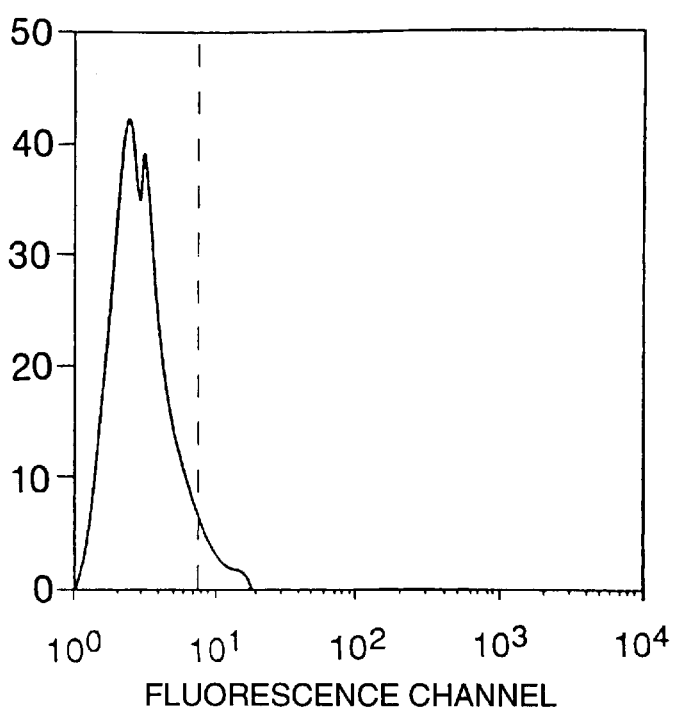
FIG._3B

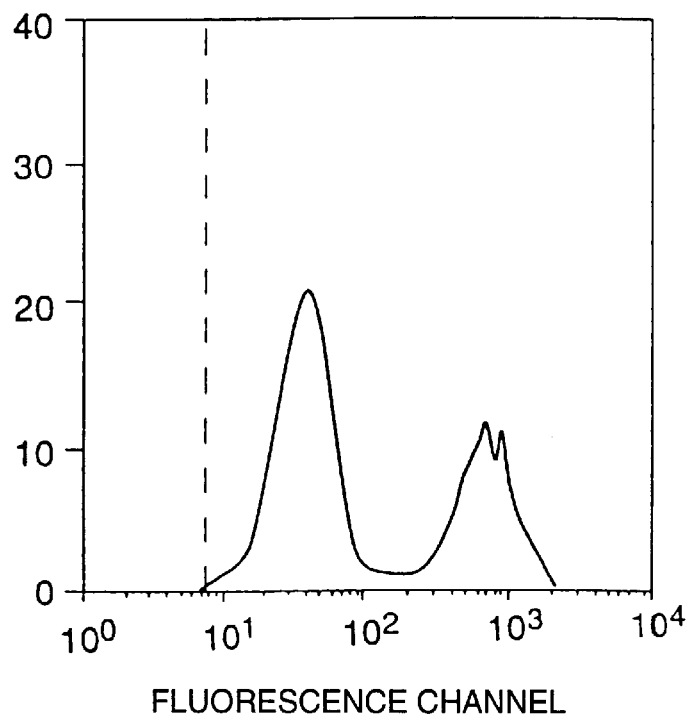
FIG._3C
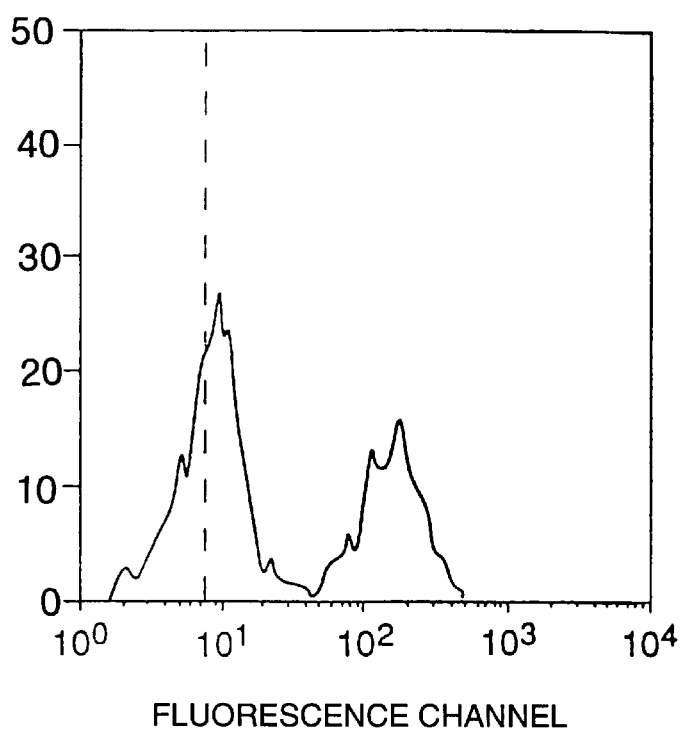
FIG._3D

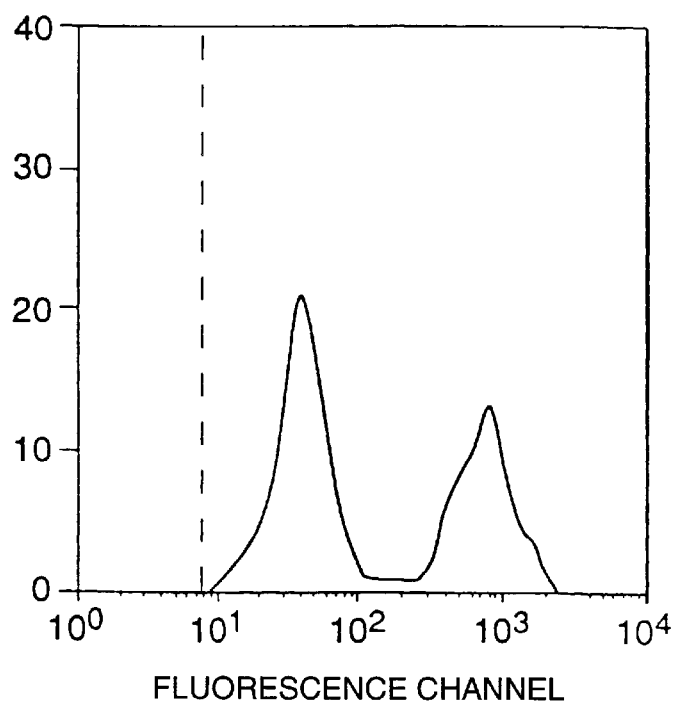
FIG._3E
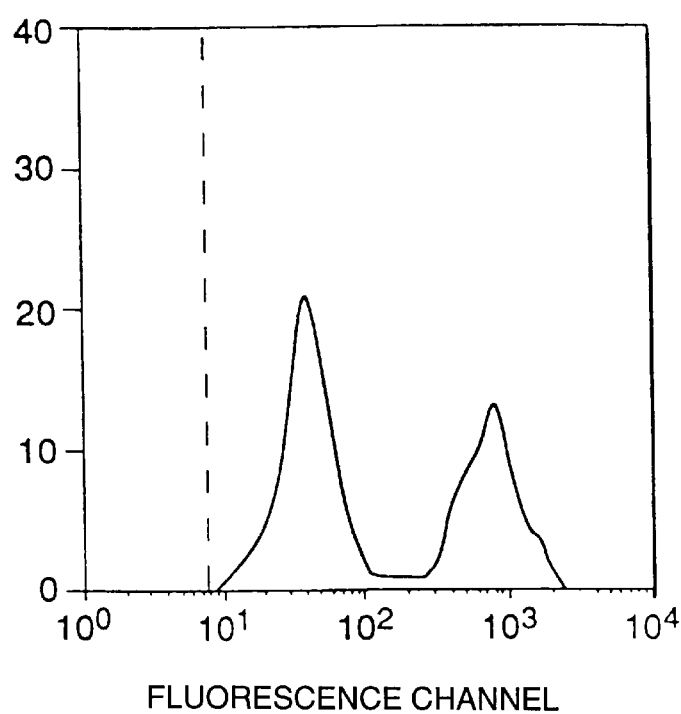
FIG._3F

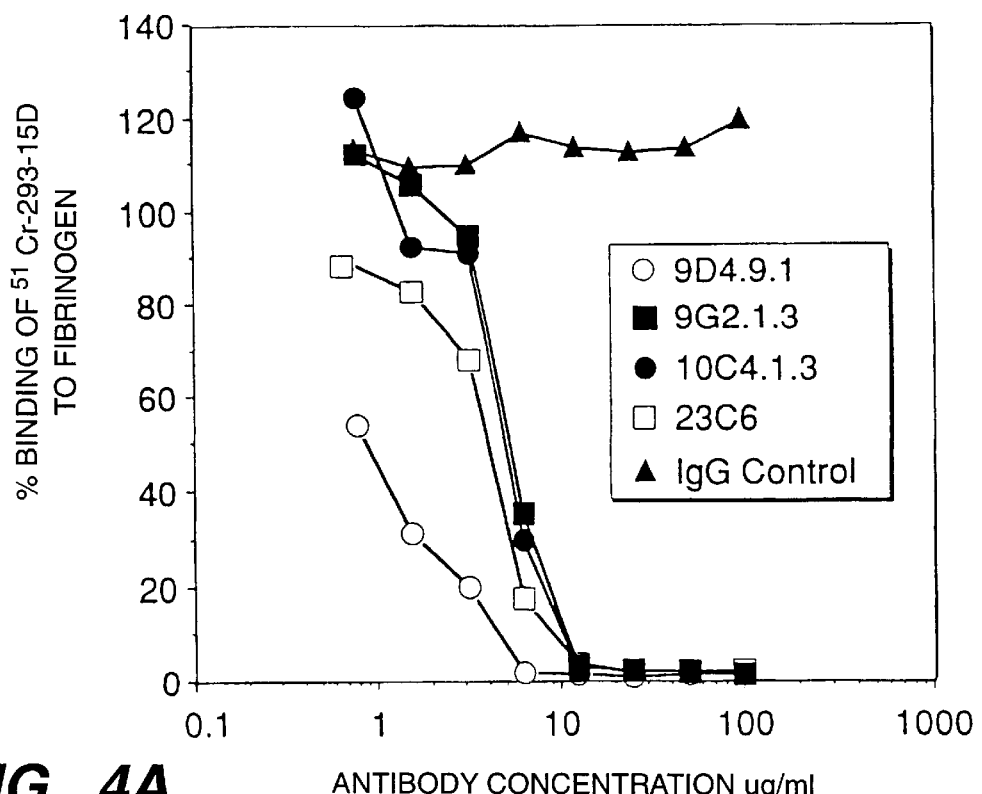
FIG._4A
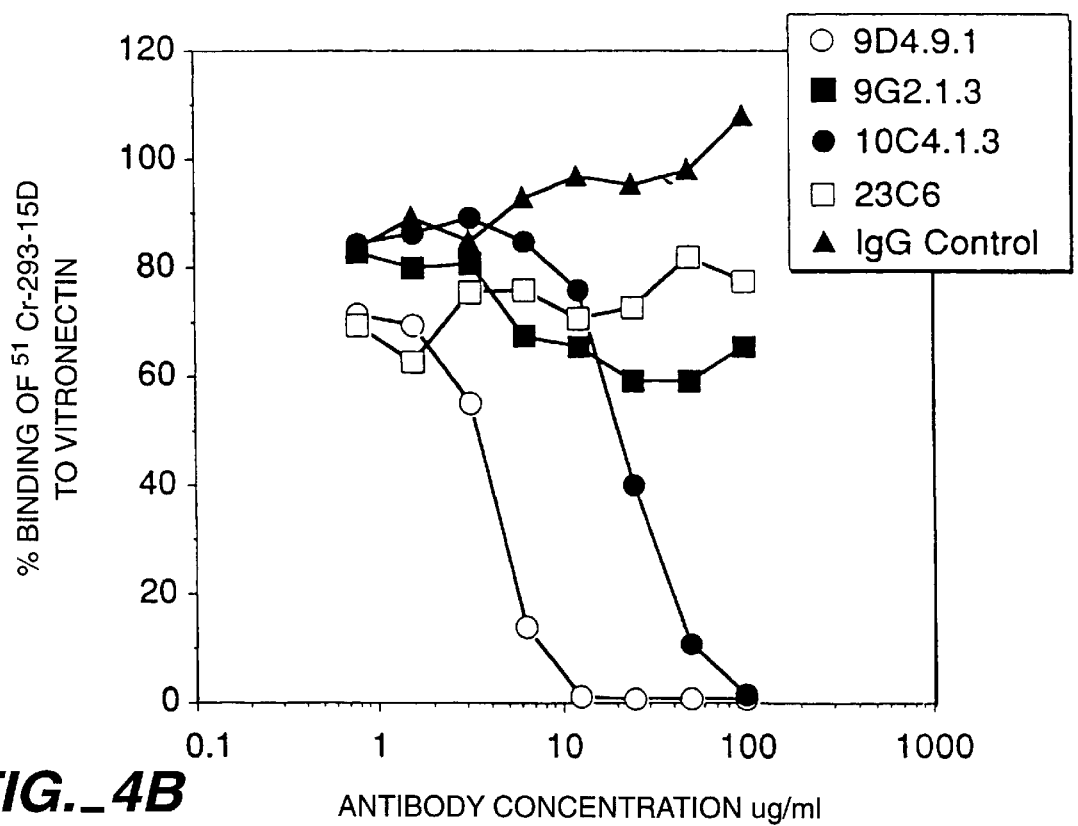
FIG._4B

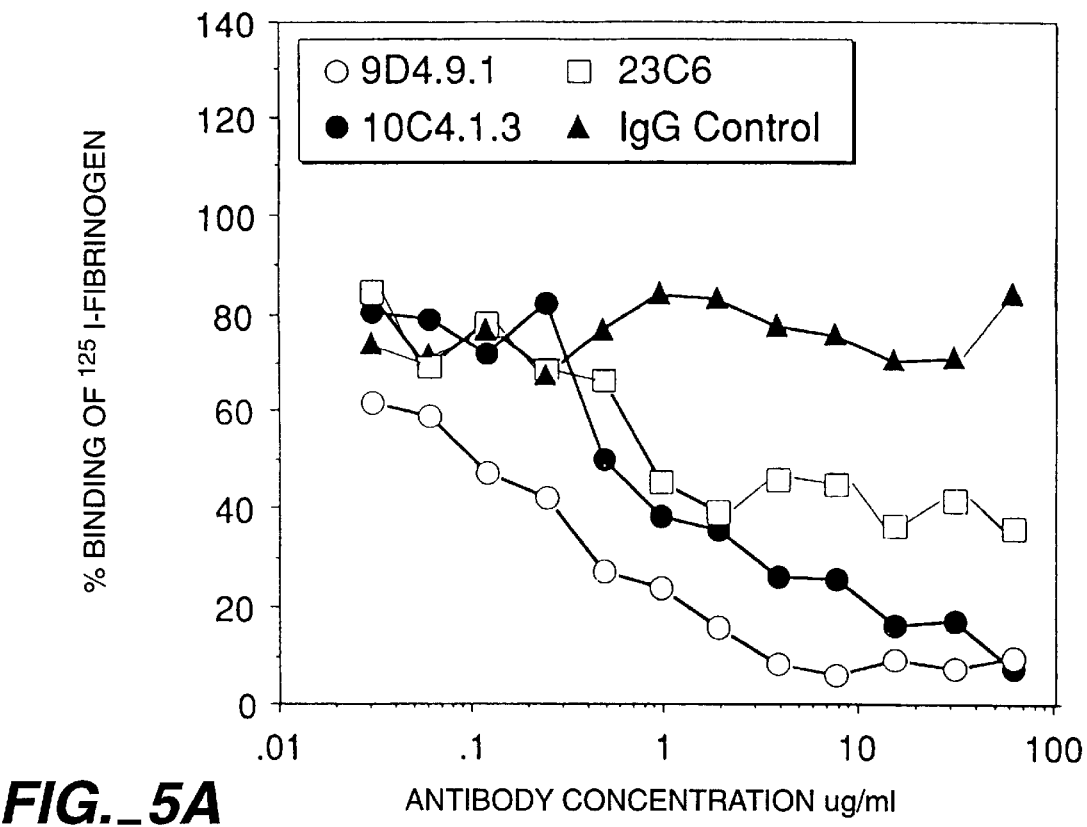
FIG._5A
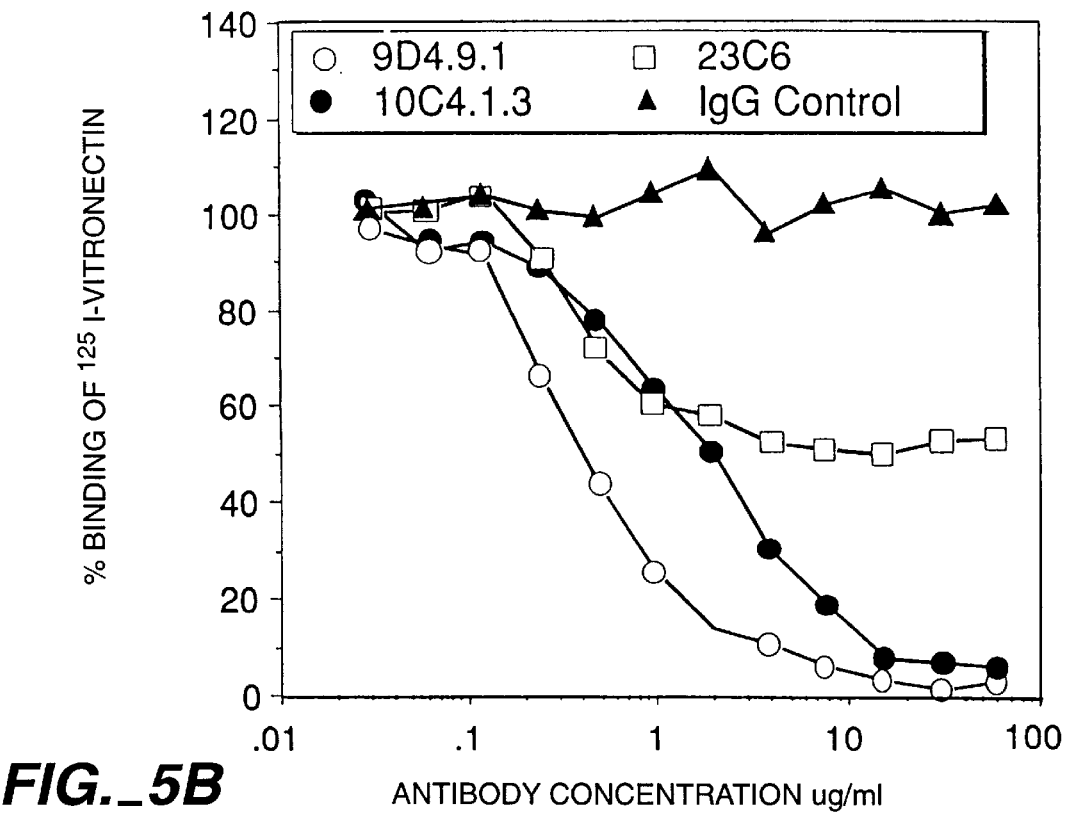
FIG._5B

ANTIBODIES TO αVβ3 INTEGRIN

This application is a continuation of U.S. application Ser. No. 08/432,618 filed May 2, 1995, now U.S. Pat. No. 5,652,110, which is related to U.S. application Ser. No. 08/432,542 filed May 2, 1995, now U.S. Pat. No. 5,652,109, which applications are continuations of U.S. application Ser. No. 08/307,844 filed Sep. 30, 1994, which application is a 371 of PCT/US93/02987 filed Mar. 30, 1993, now U.S. Pat. No. 5,578,704, which application is a continuation-in-part of U.S. application Ser. No. 08/025,913 filed Mar. 3, 1993 (abandoned), which application is a continuation of U.S. application Ser. No. 07/862,679 filed Apr. 3, 1992 (abandoned), which applications are incorporated herein by reference and to which applications priority is claimed under 35 USC §120.

FIELD OF THE INVENTION

This application relates to hybrid cell lines (lymphocyte hybridomas) for the production of monoclonal antibodies to αvβ3 integrin, to such homogeneous antibodies, and to the use of such antibodies for diagnostic and therapeutic purposes.

BACKGROUND OF THE INVENTION

αvβ3 is a member of the integrin supergene family of cell-surface lycoprotein receptors that promote cellular adhesion. Each cell has a specific repertoire of receptors that define its adhesive capabilities. The integrins are expressed as heterodimers of noncovalently associated α and β subunits. According to the nomenclature proposed by Hynes, R. O. [*Cell* 48, 875–886 (1987)], the integrins can be divided into families each with a common β-subunit and a set of variable α-subunits known to associate with the common β-subunit. The different α chains are denoted by the original cell type, by a subscript used by the original discoverer, or, as in the case of the αvβ3 receptor, by the nature of the ligand (i.e. αv stands for a vitronectin receptor α-chain). Many, but not all, integrin receptors have been shown to interact with proteins via a tripeptide sequence, Arg-Gly-Asp (or RGD using the single letter amino acid code), originally defined from studies of the cell binding domains of fibronectin [Ruoslahti, E. and Pierschbachter, M. D., *Cell* 44, 517–518 (1986); Ruoslahti, E. and Pierschbachter, M. D., *Schience* 238, 491–497 (1987)].

αvβ3 (also referred to as vitronectin receptor or VNR) is a member of the β3 integrin subfamily and is expressed on a variety of cells, including endothelial, melanoma, smooth muscle cells and, along with another integrin α2β1 (VLA-2) (the receptor for Type I collagen and laminin), on the surface of osteoclasts [Horton, M. A. and Davies, J., *J. Bone Min. Res.* 4, 803–808 (1989); Davies, J. et al., *J. Cell. Biol.* 109, 1817–1826(1989); Horton, M., *Ing. J. Exp. Pathol.* 71 741–759 (1990)]. αvβ3 mediates cell adhesion to vitronectin, fibrinogen, fibronectin, thrombospondin, osteopontin, bone sialo protein II and von Willebrand factor.

Osteoclasts are the main type of bone cells involved in the resorption of bone tissues. The resorption process involves the proliferation and chemotaxis of developing osteoclasts to the skeleton from hematopoietic sites, migration of mature cells to sites of subsequent resorption, attachment of osteoclasts to bone substrate and the eventual formation of the polarized, functional mature end cells which are directly involved in bone resorption. The αvβ3 integrin mediates adhesion of osteoclasts to RGD sequence-containing bone matrix proteins.

Antibodies to αvβ3 are expected to be valuable diagnostic and therapeutic tools in studying the biological role and the structural/functional relationships of this integrin with its various ligands. In particular, monoclonal antibodies (Mabs) detecting unique epitopes on osteoclasts would be of great value in understanding of the development of osteoclasts. Even more importantly, neutralizing Mabs specific for αvβ3 that inhibit the osteoclast binding to the bone matrix proteins have great potential as therapeutic agents useful in the treatment of conditions associated with excessive bone resorption.

There are several monoclonal antibodies known in the art that bind to various epitopes on αvβ3. Immunizing with osteoclasts from osteoclastomas (giant cell tumors of bone), Horton, M. A. et al. [*Cancer Res.* 45, 5663–5669 (1985)] produced eleven mouse hybridomas secreting monoclonal antibodies which bind to osteoclasts in normal human fetal bone and a variety of neoplastic and non-neoplastic bone lesions. One of these, designated 23C6, was subsequently shown to bind the αvβ3 complex, and was demonstrated to be able to disrupt osteoclast function [Horton, M. A. et al., *Exp. Cell. Res.* 195 368–375 (1991)]. Another monoclonal antibody, LM609 (produced in hybridoma LM609 ATCC HB 9537) disclosed in PCT Application Publication No. WO 89/05155 (published Jun. 15, 1989) and Cheresh et al. *J. Biol. Chem.* 262: 17703–17711 (1987) was also found to bind the αvβ3 complex and, due to its ability to inhibit the binding of ECr molecules present on the surface of tumor cells and blood vessel forming endothelial cells to vitronectin, fibrinogen and von Willebrand factor, was proposed for therapeutic use as tumor growth inhibitor. Monoclonal antibody 13C2(Horton, M. A. et al., *Cancel Res.* 1985, Supra) was shown to bind the αv portion of the αvβ3 molecule, whereas several other monoclonal antibodies were reported to recognize the β3 portion [Nesbitt, S. et al., Epitope Analysis of the Vitronectin Receptor (CD51), In "Leukocyte Typing IV" White Cell Differentiation Antigens, Knapp, W. et al. (eds.) 1991, p. 1037]. The specific monoclonal antibodies variously reported in the art were shown to also bind to endothelial cells and various melanoma cell lines.

There is a need for high affinity monoclonal antibodies to the αvβ3 integrin that are capable of effective inhibition of the binding of αvβ3 expressing cells to αvβ3 ligands, such as vitronectin and fibronectin.

It would be further desirable to provide monoclonal antibodies to αvβ3 that bind osteoclasts and optionally other cells known to express αvβ3.

It would be particularly desirable to provide monoclonal antibodies that are effective inhibitors of αvβ3 binding to its ligands and which specifically bind osteoclasts without binding to other cells known to express αvβ3, i.e., which are more specific for the target integrin on osteoclasts.

SUMMARY OF THE INVENTION

The present invention is based on successful research involving the production and extensive characterization of monoclonal antibodies to αvβ3 integrin. Accordingly, the present invention is directed to monoclonal antibodies, and derivatives thereof, which are capable of recognizing unique epitopes on αvβ3 and/or which exhibit high affinity for αvβ3. The invention is specifically directed to monoclonal antibodies recognizing unique epitopes on the αvβ3 complex or the β3 portion thereof. The invention is further directed to monoclonal antibodies effectively inhibiting the binding to vitronectin and fibrinogen of αvβ3 expressing cells. In a particularly important aspect, the invention is directed to monoclonal antibodies specifically binding αvβ3 on osteoclasts but not other αvβ3 on other cells (e.g. melanoma cells C32R, M-21, HA-A, HA-L and HT-144 and human umbilical vein endothelial cells).

In one aspect, the invention concerns an anti-αvβ3 monoclonal antibody that is capable of: (1) inhibiting the binding of αvβ3 expressing cells to fibrinogen, (2) binding osteoclasts, and (3) binding to substantially the same epitope recognized by any one of a monoclonal antibody selected from the group consisting of 10C4.1.3, 9G2.1.3 and 9D4.9.1 or which has an affinity for αvβ3 which is about equal to or greater than that of the foregoing three antibodies.

In another aspect, the invention concerns isolated nucleic acid encoding such antibodies, and hybridoma or recombinant cells producing such antibodies.

In a further aspect, the invention concerns the therapeutic or diagnostic use of such antibodies. The monoclonal antibodies of the invention are useful as therapeutic agents, either by themselves or in conjunction with (chemo) therapeutic agents, to treat diseases or conditions that are characterized by excessive bone resorption and/or to inhibit tumor growth. The monoclonal antibodies of the invention are also useful in diagnostic and analytical assays for determining the presence of αvβ3 on cells, cell typing and in histochemical tissue staining.

These and further aspects will be apparent from the following detailed description.

BRIEF DESCRIPTION OF THE DRAWINGS

FIGS. 3A–F is a flow cytometry comparison of Mab 23C6 αvβ3 epitopes compared with the epitopes of several Mabs of this invention. FIG. 3A shows staining of αvβ3 transformed cells with fluorescent labeled 23C6 alone, FIG. 3B depicts staining with fluorescent labeled 23C6 in competition with unlabeled 23C6, and FIGS. 3C, 3D, 3E and 3F illustrate staining with 4 Mabs of this invention in competition with labeled 23C6.

FIGS. 4A–B illustrates the ability of the Mabs to inhibit binding of αvβ3 transformed 293 cells to fibrinogen (FIG. 4A) or vitronectin (FIG. 4B). Interestingly, 23C6 could inhibit cell binding to fibrinogen, as could the other Mabs. However, 9D4.9.1 demonstrated substantially higher affinity than did any of the other Mabs tested. As shown in the lower panel, only Mabs 10C4.1.3 and 9D4.9.1 were able to substantially inhibit cell binding to vitronectin, and again the latter exhibited higher affinity than the other Mabs tested.

FIGS. 5A and 5B, respectively, depict the inhibition by various Mabs of soluble αvβ3 binding to fibrinogen and vitronectin. The results largely parallel those shown in FIGS. 4A–B.

DETAILED DESCRIPTION OF THE INVENTION

A. Definitions and General Methods

Figure 1:
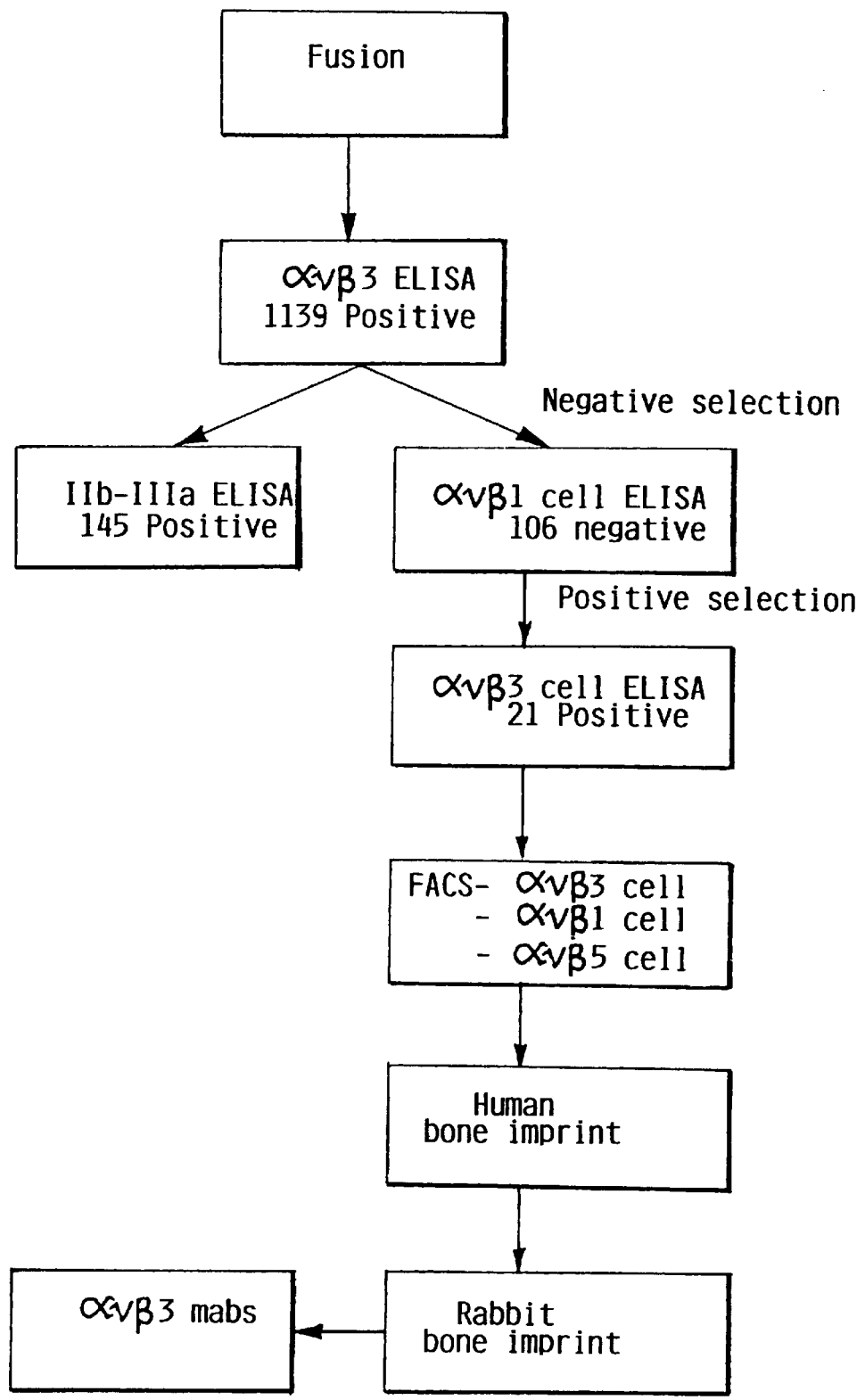
FIG. 1 is a schematic of the methods for generation of anti-αvβ3 antibodies.

The term "monoclonal antibody" as used herein refers to a substantially homogeneous population of antibodies, i.e., the individual antibodies comprising the population are identical in specificity and affinity except for possible naturally occurring mutations that may be present in minor amounts. Note that a monoclonal antibody composition may contain more than one monoclonal antibody.

The monoclonal antibodies included within the scope of the invention include hybrid and recombinant antibodies (e.g. "humanized" antibodies) regardless of species of origin or immunoglobulin class or subclass designation, as well as antibody fragments (e.g., Fab, F(ab')$_2$, and Fv), so long as they have the novel and unobvious characteristics of the antibodies described herein, in preferred embodiments being antibodies that are capable of binding to substantially the same epitope as one recognized by monoclonal antibody 10C4.1.3, 9G2.1.3 or 9D4.9.1 and/or have affinity for that epitope which is greater than or equal to the affinity of 23C6 or 9D4.9.1.

Thus, the modifier "monoclonal" indicates the character of the antibody as a substantially homogeneous population of antibodies, and is not to be construed as requiring production of the antibody by any particular method. For example, the monoclonal antibodies of the invention may be made using the hybridoma method first described by Kohler & Milstein, Nature 256:495 (1975), or may be made by recombinant DNA methods. For example, see Cabilly, et al., U.S. Pat. No. 4,816,567; or Mage & Lamoyi, in *Monoclonal Antibody Production Techniques and Applications,* pp. 79–97 (Marcel Dekker, Inc., New York, 1987).

In the hybridoma method, a mouse or other appropriate host animal is immunized with αvβ3 integrin by subcutaneous, intraperitoneal, or intromuscular routes to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell. Goding, *Monoclonal Antibodies: Principles and Practice,* p. 59–103 (Academic Press, 1986). Immunization with the extracellular domain of αvβ3 (truncated αvβ3 not containing its transmembrane or cytoplasmic domains) as shown in the examples produced a surprisingly large population of anti-αvβ3 antibodies and is believed in part to be responsible for the unique specificities and high affinities of several Mabs so identified. In addition, use of lymph node cells (rather than spleen or other tissue) as fusion partners was believed to be instrumental.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, Sand Diego, Calif. USA, and SP-2 cells available from the American Type Culture Collection, Rockville, Md. USA, or P3X63Ag8U. 1 murine myeloma cells [Yelton et al., *Curr. Top. Microbiol. Immunol.* 81, 1 (1978)]. Human myeloma and mouse-human heteromyeloma cell lines also have been described for the production of human monoclonal antibodies. Kozbor, J. Immunol. 133:3001 (1984). Brodeur, et al., *Monoclonal Antibody Production Techniques and Applications,* pp. 51–63 (Marcel Dekker, Inc., New York, 1987). As noted, the hybridomas were prepared from lymph node fusions.

Culture medium in which hybridoma cells are growing is assayed for production of monoclonal antibodies directed against the individual chains, or preferably the αvβ3 complex. Preferably, the binding specificity is determined by immunoprecipitation or by an in vitro binding assay, such as radioimmunoassay (RIA) or enzyme-linked immunoabsorbent assay (ELISA), or by FACS sorting. The monoclonal antibodies of the invention are those that bind to soluble or cell bound αvβ3 and which are neutralizing, as explained infra. Then the specificity of binding αvβ3 on various cell types is determined, with the objective being the identification of antibodies that do not bind to any other integrin than αvβ3 and, preferably, are able to discriminate between αvβ3 on melanoma tumor cells, endothelial cells and osteoclasts, i.e., are substantially specific for any one of such cell types. Substantial specificity in general means that the antibody is specific for the candidate cell type at least to the degree of discrimination shown by Mab 10C4.1.3 for osteoclasts compared to any one of cell lines C32R, M-21, HA-A, HA-L, HT-63 or MG-63. Obviously this may be expressed in terms of the quantity of antibody that binds or in other conventional measures. Finally, the screen optionally is narrowed to detect antibodies that bind to substantially the same epitope recognized by antibodies 10C4.1.3, 9G2.1.3 or 9D4.9.1 (as determined by competition assays of the sort described infra for 23C6, except that the 3 Mabs of this invention will be employed as the labelled competitive agent to determine epitope binding of the candidate). It should be kept in mind that "same epitope" does not means the exact amino acid or carbohydrate to which any of the three benchmark antibodies bind, as may be determined for example by epitope mapping using alanine scanned variants of αvβ3. "Same epitope" means the αvβ3 domain which is blocked by the binding to αvβ3 of one of the native benchmark antibodies in intact form. Of course, "same epitope" includes the αvβ3 domain residues or carbohydrate that structurally interacts or binds to the benchmark CDRs.

In a preferred embodiment of the invention, the monoclonal antibody will have an affinity which is greater than that of 23C6 and preferably is equal or greater than that of 9D4.9.1, as determined, for example, by the Scatchard analysis of Munson & Pollard, Anal. Biochem. 107:220 (1980).

The term "neutralizing antibody" as used herein refers to a monoclonal antibody that is capable of substantially inhibiting or eliminating a biological activity of αvβ3. Typically a neutralizing antibody will inhibit binding of αvβ3 to a cell matrix ligand such as vitronectin or fibrinogen to a degree equal to or greater than Mab 23C6, and preferably equal to or greater than Mabs 9D4.9.1, 10C4.1.3 or 9G2.1.3.

After hybridoma cells are identified that produce neutralizing antibodies of the desired specificity and affinity, the clones typically are subcloned by limiting dilution procedures and grown by standard methods. Goding, *Monoclonal Antibodies: Principles and Practice,* pp. 59–104 (Academic Press, 1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA is ligated into expression or cloning vectors, which are then transfected into host cells such as simian COS cells, Chinese Hamster ovary (CHO) cells, or myeloma cells that do not otherwise produce immunoglobulin protein. The transformant cells are cultured to obtain the synthesis of monoclonal antibodies in the recombinant host cell culture.

The DNA optionally is modified in order to change the character of the immunoglobulin produced by its expression. Immunoglobulin variants are well known. For example, chimeric antibodies are made by substituting the coding sequence for human heavy and light chain constant domains in place of the homologous murine sequences, Cabilly et al. op cit, or Morrison, et al., Proc. Nat. Acad. Sci. 81:6851 (1984). In addition, the Fc domain chosen is any of IgA, IgD, IgE, IgG-1, -2, -3 or -4, or IgM. The Fc domain optionally is capable of effector functions such as complement binding.

Humanized forms of the murine antibodies are made by substituting the complementarity determining regions of the mouse antibody into a human framework domain, e.g., see PCT Pub. No. WO92/22653, published Dec. 23, 1992. In some embodiments, selected murine framework residues also are substituted into the human recipient immunoglobulin.

Fusions of the immunoglobulin of this invention and cytotoxic moieties are made, for example, by ligating to the immunoglobulin coding sequence all or part of the coding sequence for a cytotoxic non-immunoglobulin polypeptide. Such non-immunoglobulin polypeptides include polypeptide toxins such as ricin, diphtheria toxin, or Pseudomonas exotoxin.

Also, the conjugates can be prepared by in vitro methods. For example, immunotoxins may be constructed using a disulfide exchange reaction or by forming a thioether bond between the immunoglobulin and the toxin polypeptide. Examples of suitable reagents for this purpose include iminothiolate and methyl-4-mercaptobutyrimidate. In addition, other fusions are readily produced by similar recombinant methods. Suitable fusion partners for the immunoglobulin of this invention include viral sequences, cellular receptors such as the T-cell receptor, cytokines such as TNF, interferons, or interleukins, and other biologically or immunologically active polypeptides. Typically such non-immunoglobulin fusion polypeptides are substituted for the constant domains of an antibody of the invention. Alternatively, they are substituted for the variable domains of one antigen-combining site of an antibody of the invention.

Substitution of the Fr or CDRs of an antibody having specificity for a non αvβ3 antigen will create a chimeric bivalent antibody comprising one antigen-combining site having specificity for αvβ3 and another antigen-combining site having specificity for a different antigen. In such embodiments, the light chain is deleted and the Fv of the heavy chain is substituted with the desired polypeptide. These antibodies are termed bivalent or polyvalent, depending upon the number of immunoglobulin "arms" possessed by the Fc domain employed (IgMs will be polyvalent). Aside from the nonimmunoglobulins mentioned above, the antibody also is rendered multivalent by recombination of antibodies having more than one specificity. For instance, the antibody in some embodiments is capable of binding αvβ3 as described elsewhere herein but is also capable of binding a T-cell determinant such as CD3, CD4, CD8, CD18, CD11a, CD11b or CD11c. These other antibodies are well known. The multispecific, multivalent antibodies are made by cotransforming a cell with DNA encoding the heavy and light chains of both antibodies and the proportion of expressed antibodies having the desired structure recovered by immunoaffinity chromatography or the like. Alternatively, such antibodies are made from monovalent antibodies which are recombined in vitro in conventional fashion.

Monovalent antibodies also are made by techniques that are conventional per se. Recombinant expression of light chain and a modified heavy chain is suitable. The heavy chain is truncated generally at any point in the Fc region so as to prevent heavy chain crosslinking. Alternatively, the relevant cysteines are substituted with another residue or deleted so as to prevent crosslinking. In vitro methods also are used to produce monovalent antibodies, e.g., Fab fragments are prepared by enzymatic cleavage of intact antibody.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; radioactive isotopic labels, such as, e.g., $^{125}I$, $^{32}P$, $^{14}C$, technicium, or $^3H$, or an enzyme, such as alkaline phosphatase, beta-galactosidase or horseradish peroxidase.

Any method known in the art for separately conjugating the antibody to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques,* pp. 147–158 (CRC Press, Inc., 1987).

Competitive binding assays rely on the ability of a labeled standard (which may be αvβ3 or an immunologically reactive portion thereof) to compete with the test sample analyte (αvβ3) for binding with a limited amount of antibody. The amount of αvβ3 in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, or the protein to be detected. In a sandwich assay, the test system analyte is bound by a first antibody which is immobilized on a solid support, and thereafter a second antibody binds to the analyte, thus forming an insoluble three part complex. David & Greene, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The antibodies of the invention also are useful for in vivo imaging, wherein an antibody labeled with a detectable moiety such as a radio-opaque agent or radioisotope is administered to a host, preferably into the bloodstream, and the presence and location of the labeled antibody in the host is assayed. This imaging technique is useful in the staging and treatment of neoplasms or bone disorders. The antibody may be labeled with any moiety that is detectable in a host, whether by nuclear magnetic resonance, radiology, or other detection means known in the art.

The neutralizing antibodies of the invention are especially useful in therapeutic applications, to prevent or treat unwanted bone resorption, or tumor cell growth or metastasis. Obviously, Mabs of the 10C4.1.3 type are not useful for treating or in vivo imaging of tumors of the same type described in Table 2 infra since they do not bind to αvβ3 found on such cells. Instead these Mabs are especially useful of treating conditions of bone resorption or degradation, for example as found in osteoporosis or resulting from PTHrP over-expression by some tumors.

For therapeutic applications, the antibodies of the invention are administered to a mammal, preferably a human, in a pharmaceutically acceptable dosage form. They are administered intravenously as a bolus or by continuous infusion over a period of time, by intramuscular, subcutaneous, intra-articular, intrasynovial, intrathecal, oral, topical, or inhalation routes. When the antibody possesses the suitable activity it is also suitably administered by intratumoral, peritumoral, intralesional, or perilesional routes, to exert local as well as systemic therapeutic effects.

Such dosage forms encompass pharmaceutically acceptable carriers that are inherently nontoxic and nontherapeutic. Examples of such carriers include ion exchangers, alumina, aluminum stearate, lecithin, serum proteins, such as human serum albumin, buffers such as phosphate or glycine, sorbic acid, potassium sorbate, partial glyceride mixtures of saturated vegetable fatty acids, water, salts, or electrolytes such as protamine sulfate, sodium chloride, metal salts, collodial silica, magnesium trisilicate, polyvinyl pyrrolidone, cellulosic polymers, and polyethylene glycol. Carriers for topical or gel-based forms of antibody include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. Conventional depot forms include, for example, microcapsules, nano-capsules, liposomes, plasters, sublingual tablets, and polymer matrices such as polylactide:polyglycolide copolymers. When present in an aqueous dosage form, rather than being lyophilized, the antibody typically will be formulated at a concentration of about 0.1 mg/ml to 100 mg/ml, although wide variation outside of these ranges is permitted.

For the prevention or treatment of disease, the appropriate dosage of antibody will depend on the type of disease to be treated, as defined above, the severity and course of the disease, whether the antibodies are administered for preventive or therapeutic purposes, the course of previous therapy, the patient's clinical history and response to the antibody, and the discretion of the attending physician. The antibody is suitably administered to the patient at one time or over a series of treatments.

Depending on the type and severity of the disease, about 0.015 to 15 mg of antibody/Kg of patient weight is an initial candidate dosage for administration to the patient, whether, for example, by one or more separate administrations, or by continuous infusion. For repeated administrations over several days or longer, depending on the condition, the treatment is repeated until a desired suppression of disease symptoms occurs. However, other dosage regimens may be useful and are not excluded herefrom.

According to another embodiment of the invention, the effectiveness of the antibody in preventing or treating disease may be improved by administering the antibody serially or in combination with another agent that is effective for the same clinical objective, such as another antibody directed against a different epitope than the principal antibody, or one or more conventional therapeutic agents known for the intended therapeutic indication, e.g. prevention or treatment of conditions associated with excessive bone resorption such as, osteoporosis or inhibition of tumor cell growth or metastasis.

The antibodies of the invention also are useful as affinity purification agents. In this process, the antibodies against $\alpha v \beta 3$ are immobilized on a suitable support, such a Sephadex resin or filter paper, using methods well known in the art. The immobilized antibody then is contacted with a sample containing the $\alpha v \beta 3$ to be purified, and thereafter the support is washed with a suitable solvent that will remove substantially all the material in the sample except the $\alpha v \beta 3$, which is bound to the immobilized antibody. Finally, the support is washed with another suitable solvent, such as glycine buffer, pH 5.0, that will release the $\alpha v \beta 3$ from the antibody.

The following examples are offered by way of illustration only and are not intended to limit the invention in any manner.

EXAMPLE 1

A. Generation of Mabs Specific for Human $\alpha v \beta 3$

To produce Mabs specific for $\alpha v \beta 3$ integrin, Balb/c mice were immunized with $\alpha v \beta 3$ integrin purified from 293-15D cell line expressing $\alpha v \beta 3$ complex which were generated by transfecting 293 cells (ATCC CRL 1573) with DNAs prepared from PMNCV vector expressing $\alpha v$ or $\beta 3$ plus DNA coding for Neomycin resistance gene. $\alpha v \beta 3$ was purified from an NP 40 cell lysate of 293-15D cells by using a lentil lectin column. The purity of the $\alpha v \beta 3$ prepared was then confirmed by isoelectrophoresis. Mice were immunized into foot pads once with 5 $\mu$g of $\alpha v \beta 3$ emulsified in MPL/TDM adjuvant (Ribi Immunochem. Research Inc., Hamilton, Mont.) and then subsequently six times with 5 mg of $\alpha v \beta 3$ immersified in MPL/TDM adjuvant at 2 week intervals. Three days after the last immunization, lymph node cells from these mice were fused with P3X63Ag8U.1 myeloma cells (Yelton, et al., *Curr. Top. Microbiol. Immunol.* 81:1, 1978) using 35% polyethylene glycol as described (Yarmush et al, *Proc. Nat. Acad. Sci.* 77:2899, 1980). The remainder of the process is depicted in FIG. 1. Hybridoma cell lines were selected for anti-$\alpha v \beta 3$ antibody production by their ability to bind soluble $\alpha v \beta 3$ by ELISA and to bind cell lines expressing various integrins by Flow microfluorometry analysis using FACSCAN (Becton Dickinson FACS systems, Mountain View, Calif.). Isotypes (Table 1) of these positive Mabs were determined by ELISA using isotype specific alkaline phosphatase-conjugated goat anti-mouse immunoglobulin (Harlow and Lane, Antibodies: A Laboratory Manual, p.597, Cold Spring Harbor Laboratory, 1988).

TABLE I

| Characteristics of Mabs | | | | |
|---|---|---|---|---|
| Cell Line | Isotype | Immunoblot | Immune ppt | Epitope |
| 9D4.9.1 | IgG1, K | − | + | $\beta 3$ |
| 9G2.1.3 | IgG2a, K | − | + | $\alpha v \beta 3$ |
| 10C4.1.3 | IgG1, K | − | + | $\alpha v \beta 3$ |

Positive hybridoma cell lines were subcloned twice by limiting dilution technique.

Figure 2:
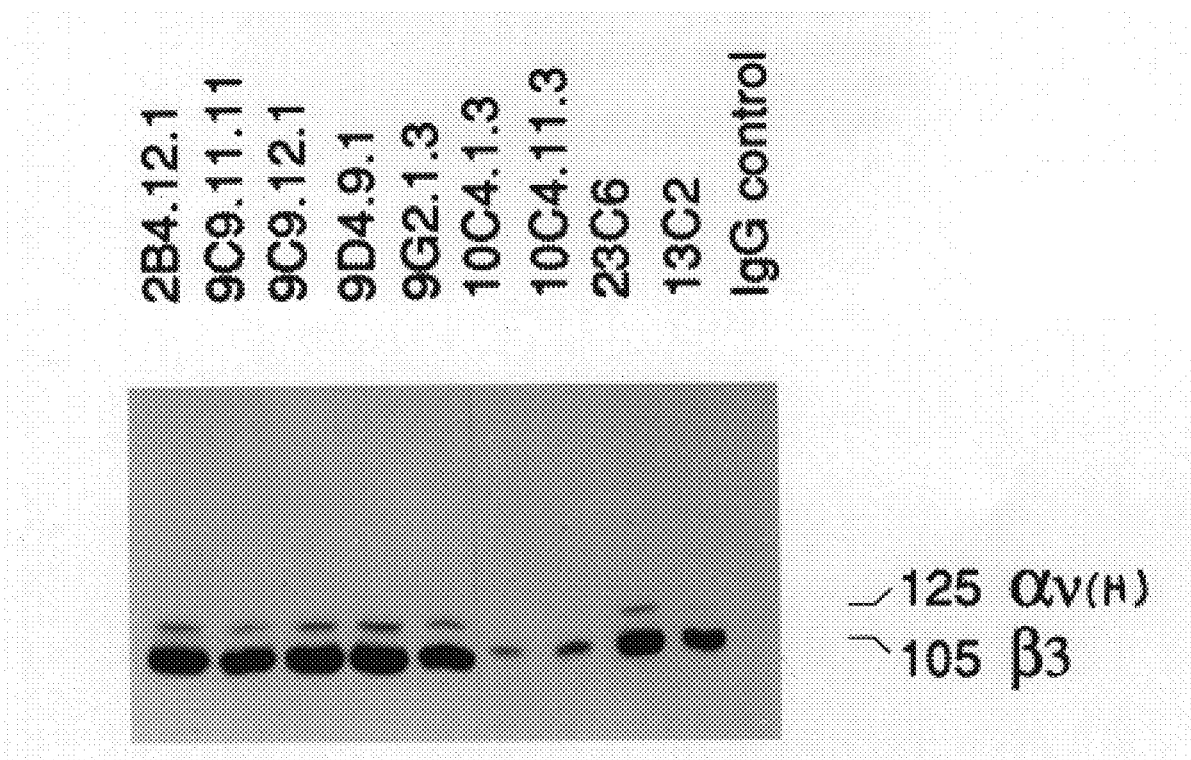
FIG. 2 depicts an immunoprecipitation of αvβ3 components using the antibodies of this invention, two positive controls (23C6 and 13C2) and an IgG negative control.

B. Immune Precipitation of $\alpha v \beta 3$ Complex with Mabs 293-15D transfectants grown F12/DMEM medium with 10% FCS were harvested by treatment with EDTA and biotinylated by using NHS-LC-Biotin. Cells (5×10$^6$ cells/ml) were incubated with 1 $\mu$g/ml of NIH-LS-Biotin for 1 hour at room temperature. The unbound biotin was then removed by washing in 0.05 mM tris buffer containing 0.5M NaCl m 1 mm. CaCl2 and 1 m N MgCl2 (cell wash buffer). Cells were lysed by treatment with 1% NP-40 and cell debris were removed by microcentrifugation for 10 min. The supernatant was used for the immunoprecipitation. Fifty $\mu$l of Protein-G in 0.05 M tris buffer containing 0.5 M NaCl and 0.1% Tween-20 (IP wash buffer) were incubated with 100 $\mu$l of Mabs (100 $\mu$g/ml) for 30 min at room temperature. After washing twice in IP wash buffer, nonspecific binding sites on Protein-G were blocked with 1% BSA for 1 hr. at room temperature, washed twice and incubated with the supernatant containing biotinylated membrane proteins for 1 hr at room temperature. The complex was washed six times, reduced in SDS PAGE-sample buffer containing 2-ME by boiling and analyzed by electrophoresis using 12% SDS polyacrylamide gel. FIG. 2 depicts the results.

EXAMPLE 2

Cell Culture and Immunofluorescence Staining of Various Tissues

Transfected cells and tumor cells grown in F12/DMEM medium (1:1 o/o mixture) containing 10% FCS, glutamine and antibiotics were washed three times in the cell sorter buffer (CSB, PBS containing 1% FCS and 0.01% NaN3) by centrifugation at 1,000 rpm for 5 min and resuspended to be 4×10$^6$ cells/ml in CSB. Twenty five $\mu$l of cells were added into a 96 well U-bottom plate and incubated with 100 $\mu$l of antibodies for 30 min on ice. At the end of the incubation, cells were washed twice in CSB and the Mab bound onto cells were detected by incubating cells with FITC conjugated goat anti-mouse Ig antibodies for 30 min on ice. Cells were washed twice in CSB, resuspended in 0.5 ml of CBS, and analyzed by Flow microfluorometry as described (Loken, et al. *Ann. N.Y. Acad. Sci.* 254:163-; Miller, et al., *Rev. Sci. Instrum.* 49:1137–9, 1978). The results are shown in Table 2.

TABLE 2

Flow microfluorometry analysis of mabs with various cells

|  | 2B4.12.1 | 9C9.11.11 | 9C9.12.1 | 9D4.9.1 | 9G2.1.3 | 10C4.1.3 | 23C6 |
|---|---|---|---|---|---|---|---|
| Transfected Cells |  |  |  |  |  |  |  |
| 293 | − | − | − | − | − | − | − |
| 293-52B (αvβ1) | − | − | − | − | − | − | − |
| 293-15D (αvβ3) | +++ | +++ | +++ | +++ | +++ | +++ | +++ |
| 292-CLB (IIb-IIIa) | +++ | +++ | +++ | +++ | + | − | ++ |
| Human Melanomas |  |  |  |  |  |  |  |
| C32R | ++ | ++ | ++ | ++ | ++ | − | ++ |
| M-21 | ++ | ++ | ++ | ++ | ++ | + | ++ |
| HA-A | ++ | ++ | ++ | ++ | ++ | − | ++ |
| HA-L | ++ | ++ | ++ | ++ | ++ | − | ++ |
| HT-144 | ++ | ++ | ++ | ++ | ++ | − | ++ |
| Osteosarcoma (MG-63) | + | + | + | + | + | − | − |
| Human Umbilical Vein Endothelium | + | + | + | + | + | − | + |
| Human Osteoclasts* | +++ | +++ | +++ | +++ | +++ | +++ | +++ |

FACS Results Graded: − (Mean FL Channel 0–10). + (Mean FL Channel 10–100). ++ (Mean FL Channel 100–1000), +++ (Mean FL Channel >1.000)
*Tissue Frozen Section (Osteoclastoma), tissue section results graded: + (weak). ++ (moderate), +++ (strong).

Table 2 depicts the determination of the portion of αvβ3 recognized by these Mabs by FACS analysis of transfected cells expressing different integrins as well as by ELISA using soluble integrin proteins. Mab 9G2.1.3 bound strongly to 293-15D expressing αvβ3 and very weakly to 293-CLB expressing IIb–IIIa, but not 293-52B expressing αvβ3. Mab 10C4.1.3 only bound to 293-15D but not others. Therefore, it was concluded that these two Mabs (9G2.1.3 and 10C4.1.3) recognized αvβ3. In contrast, Mab 9D4.9.1 strongly bound to both 293-15D as well as 293-CLB but not 293-52B. Thus, the Mab 9D4.9.1 was concluded to the bind β3 portion of αvβ3.

Table 2 also shows that Mab 9C9.11.11 bound to osteoclasts, human endothelial cells and various melanoma cells. This staining pattern is similar to that of 23C6. In contrast, Mab 10C4.1.3 recognized only osteoclasts, suggesting a surprising and very narrow specificity. The staining pattern of Mabs 9D4.9.1 and 9G2.1.3 for human melanoma tumor cells, glioma cells and normal endothelial cells were similar to that of Mab 23C6: these Mabs recognized various human melanoma cells, and osteoclasts strongly, and human osteosarcoma MG-63 cells and human endothelial cells weakly. In contrast Mab 10C4.1.3 showed a strong binding to human osteoclasts and a weak binding to one of the human myeloma cells, M-21, but no binding to other cells. These results suggest that 10C4.1.3 recognizes an epitope unique to human osteoclasts.

EXAMPLE 3

Determination of Epitopes by Competitive Immunofluorescence Staining

αvβ3 transfected 293-15D cells (1×10$^5$ cells/100 μl) were incubated with 100 μl of the first purified Mab for 30 min on ice, washed twice and incubated with the second Mab, FITC conjugated Mab 23C6 for 30 min. At the end of the incubation, cells were washed twice in CSB and resuspended in 0.5 ml of CBS and the level of FITC conjugated Mab 23C6 binding on 293-15D cells was examined by flow microfluorometry (FACSCAN). The results are depicted in FIG. 3. Panels are as follows:

(3A) NONE+FL-23C6 (shaded area represents unstained cells)

(3B) 23C6+FL-23C6

(3C) 9D4.9.1+FL-23C6

(3D) 9G2.1.3+FL-23C6

(3E) 10G4.1.3+FL-23C6

(3F) IgG+FL-23C6

Several Mabs which recognize the α-chain of αvβ3 designated as CD51, or β-chain of vitronectin receptors, CD61, have been described (Nesbitt et al, 1991, in "Leukocyte typing IV, p1037). More recent study (Horton, *Int. Exp. Pathol.,* 71:741 [1990]) showed that Mab 23C6 and LM609, which were grouped as Mabs recognizing the β epitope of CD51, may recognize the intact αvβ3 complex. Thus to confirm that the Mabs binding to the αvβ3 complex recognize different epitopes from that of 23C6, the staining of 293-15D with fluoresceinated 23C6 was examined in the presence of 100 fold higher level of unlabeled Mabs and analyzed by FACSCAN. The results in FIG. 3 showed that Mabs 9D4.9.1 and 10C4.1.3 did not interfere at all with the binding of fluoresceinated-23C6 to 15D cells. In the same experiment, the same amount of unlabeled 23C6 completely inhibited the binding of F-23C6 while the irrelevant control Mab did not have any effect. Thus it was confirmed that at least these two Mabs indeed recognize epitopes different from those recognized by 23C6. In contrast, Mab 9G2.1.3 at high concentration, has some inhibitory effect on the F-23C6 binding but could not completely block the F-23C6 binding. Thus it is concluded that Mab 9G2.1.3 recognizes a different epitope from the one recognized by F-23C6, but these epitopes appear to be closely orientated. Since it has reported that LM 609 (Cheresh, et al., *J. Biol. Chem.,* 262:17703–17711 [1987]) recognizes the same epitope as 23C6 it is concluded that our Mabs recognized different epitopes from the one recognized by Mab LM 609.

EXAMPLE 4

Inhibition of the Binding of 293-15D Cells to Ligands (Fibrinogen and Vitronectin) by Mabs Microplates (NUNC, Breakapart C8 Maxi Sorp) were coated with 100 μl/well 10 μg/ml of fibrinogen or vitronectin overnight at 4° C. After being washed three times in PBS, plates were blocked with 1% BSA in PBS for 1 hr and then were incubated with various concentrations of Mabs for 30 min followed by the addition of 100 ml of $^{51}$Cr labeled 293-15D cells. Plates were centrifuged at 600 rpm for 2 min and incubated for 90 min at 37° C. At the end of the incubation, plates were washed three times and $^{51}$Cr labeled 293-15D cells bound to the ligand were counted by a gamma counter. $^{51}$Cr labeled 293-15D transfectants expressing αvβ3 were prepared as follows. Cells were grown in F12/DMEM medium containing 10% FCS, 0.1% glucose and 2 mM glutamine for 40 hr, were harvested by treatment with 10 mM EDTA in PBS for 2 min, washed twice in PBS and resuspended to be 5×10$^7$ cells/ml in culture medium without FCS. 0.5 ml of 293-15D cells were then incubated with 250 mCi $^{51}$Cr and for 1 hr at 37° C. At the end of the incubation, excess unbound $^{51}$Cr was removed by washing three times in F12/DMEM medium and resuspended to be 6×10$^5$ cell/ml in culture medium without FCS. FIGS. 4A–B depicts the results.

The top panel of FIG. 4 shows the binding of $^{51}$Cr-293 15D to fibrinogen coated wells in the presence of various concentration of Mabs. All three Mabs inhibit the binding of $^{51}$Cr-293 15 D to fibrinogen very effectively. The strongest inhibition was shown with Mab 9D4.9.1. The bottom panel shows the binding of $^{51}$Cr-293 15D to vitronectin coated wells. Under the conditions tested, 9D4.9.1 and 10C4.1.3 could inhibit this interaction but 9G2.1.3 and 23C6 showed a very weak inhibition, if any. In general, it was harder to inhibit the interaction between αvβ3 transfected cells to vitronectin than the interaction between αvβ3 transfected cells to fibrinogen.

EXAMPLE 6

Inhibition of αvβ3 integrin Binding to Fibrinogen and Vitronectin by Monoclonal Antibodies Microtiter plates were coated with 100 μl/well of 10 μg/ml of purified fibrinogen or vitronectin, overnight at 4° C. After washing three times in PBS, the plates were blocked with 1% BSA for 1 hour at room temperature. After washing the plate in PBS, $^{51}$Cr-293-15D cells preincubated with various concentrations of Mabs for 30 minutes on ice were transferred to the ligand coated plate. The plates were then centrifuged at 600 rpm for 2 minutes and incubated for 90 minutes at 37° C. At the end of the incubation, the plates were washed three times in PBS and the $^{51}$Cr labeled 293-15D cells bound to the ligand were counted by a gamma counter. The results, which parallel those in Example 4, are depicted in FIGS. 5a and 5b.

EXAMPLE 7

Histochemical Staining of Frozen Sections of Human Tissues and Bone Imprints

Frozen sections of human osteoclastoma tumors and bone imprints from human fetal limb bones (14 weeks gestation), newborn rabbit and rat bone, embryonic chick bone and adult red deer antler, and from the following tissues of adult human origin (liver, kidney, pancreas, colon, ileum, heart, lung, thymus, tonsil, spleen, placenta, skin, uterine cervix, umbilical cord, breast carcinoma, malignant melanoma, smears of peripheral blood and bone marrow mononuclear cells) were prepared as described [Horton, M. A. et al., Cancer Res. 45, 5663–5669 (1985)]; these were air-dried, fixed in acetone for 10 minutes at room temperature and stored at −20° C. until use. Slides were brought to room temperature, rehydrated in PBS then incubated with 150 μl of 1% FCS/PBS containing 1 μg of purified Mabs for one hour. After washing in 1% FCS/PBS the slides were incubated sequentially with biotinylated anti-mouse Ig and then with avidin-biotin-horseradish peroxidase complex at the manufacturer/s recommended dilutions (Vector Lab, Burlingame, Calif.) for one hour. After further washes, the bound peroxidase was developed in 0.1 mg/ml diaminobenzidine tetrahydrochloride containing 0.07% $H_2O_2$ (Organon Teknina Corp. Durham, N.C.) in pBS and counter stained with 0.5% methyl green for 5 minutes. The slides were then dehydrated in graded alcohols, then cleared in xylene and mounted in permountant (Fisher Scientific Co., San Francisco, Calif.) for microscopy.

Figure 6A:
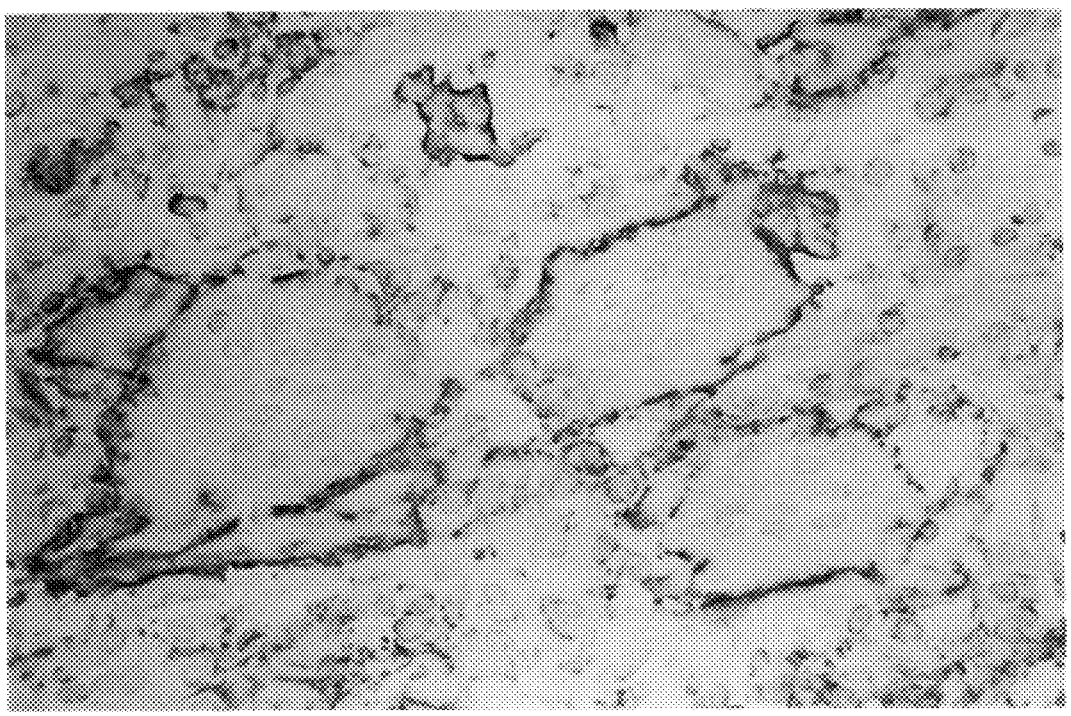
FIGS. 6A–B shows the immunoperoxidase histochemical staining of human osteoclasts (multinucleated cells) from giant cell tumor of bone. 6A: Mab 10C4.1.3. 6B: IgG control antibody. Pictures were taken at 330×magnification.
Figure 6B:
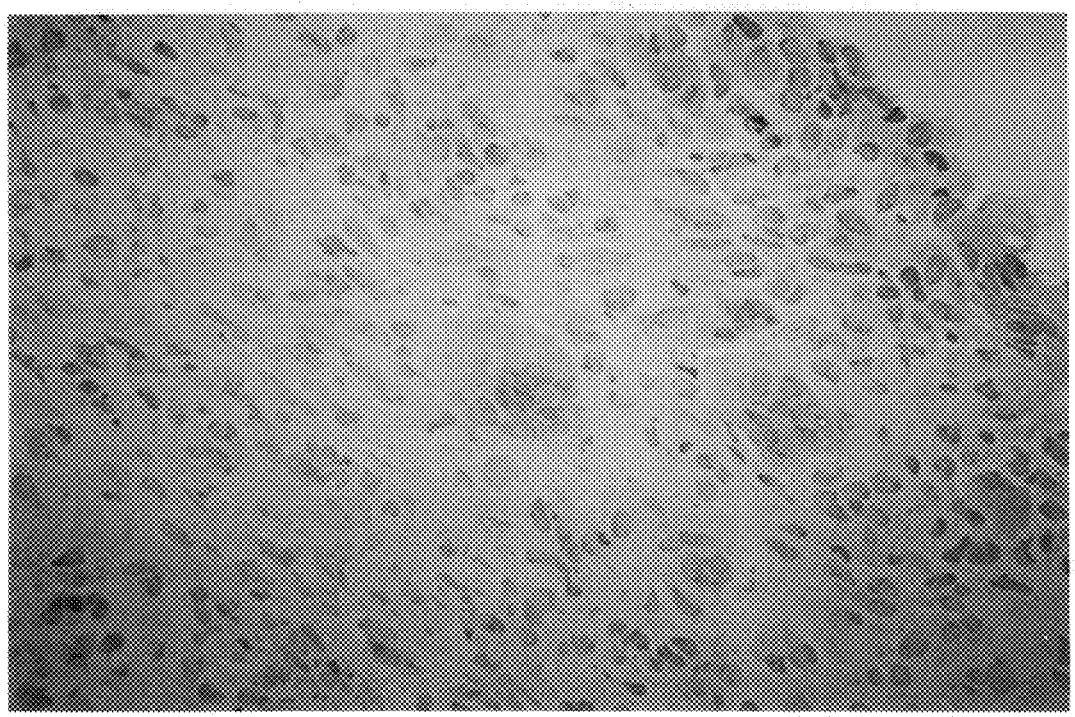

FIG. 6 shows clear membrane staining of multinucleated osteoclasts from human bone imprints and frozen sections of giant cell tumor of bone using Mab 10C4.1.3; a control Mab did not show staining. Mabs 9D4.9.1 and 9G2.1.3 showed a similar staining pattern to Mab 10C4.1.3. None of the Mabs recognized osteoclast vitronectin receptor in conventional formalin-fixed and paraffin-embedded tissue sections.

We have examined the binding of these Mabs to osteoclasts present in the bone imprints from rat, rabbit, chicken and deer in comparison to human.

Bone imprints were stained with mAbs followed by F-goat anti-mouse IgG. The level of fluorescence staining was examined by fluorescent microscopy and graded as weak (+), moderate (++) and strong (+++) or absent (−).

TABLE 3

Determination of the mAb binding to osteoclasts from various species

| mAb | 9D4.9.1 | 9G2.1.3 | 10C4.1.3 | 23C6 |
|---|---|---|---|---|
| Species | | | | |
| Human | +++ | +++ | +++ | +++ |
| Rat | − | − | − | − |
| Rabbit | − | +++ | − | +++ |
| Chicken | − | +++ | − | +++ |
| Deer | − | ++ | − | +++ |

Mab 9G2.1.3 recognizes osteoclasts from rabbit, chicken, deer in addition to human; this distribution is similar to that seen with 23C6 (Horton et al., 1985, op. cit.). In contrast, Mabs 9D4.9.1 and 10C4.1.3 only recognized human osteoclasts; to date, no αvβ3 complex-specific Mabs have shown such species selectivity.

The distribution of the antigens recognized by the three Mabs was analyzed by immunohistochemistry on frozen sections from the above-listed tissues of normal adult and fetal origin (data not shown). Mab 9D4.9.1 stained platelets (and megakaryocytes in bone marrow) intensely in all tissues studied. In addition, vascular endothelium was stained, variably and weakly, in all tissues. Mab 9G2.1.3 also stained vascular endothelium, but failed to react with platelets and megakaryocytes. Both antibodies stained kidney (glomerulus, tubules(, hepatic sinusoids, colonic and ileal smooth muscle, placenta (cyto- and syncytiotrophoblasts) and neoplastic melanocytes in malignant melanoma. In contrast, Mab 10C4.1.3 failed to stain or give a much weaker reaction in tissues recognized by Mab 9G2.1.3 For example, Mab 10C4.1.3 did not stain intestinal smooth muscle or placenta.

The antigenic specificities recognized by these Mabs were further investigated by examining their binding to various cell lines including human melanoma tumor cells, osteosarcoma cells and normal human umbilical vein endothelial cells (HUVEC) by flow microfluorometry. Mabs 9D4.9.1 and 9G2.1.3 bound strongly to various human melanoma cells and less to MG-63 human osteosarcoma cells and HUVEC. In contrast, Mab 10C4.1.3 bound weakly to only one of the human melanoma cell lines, M-21. These results further confirm that 10C4.1.3 recognizes a novel antigenic epitope.

The following antibody producing hybridomas have been deposited with the American Type Culture Collection, 10801 University Blvd., Manassas, Va. 20110-2209, USA (ATCC):

| Antibody | ATCC Dep. No. | Deposit Date |
|---|---|---|
| 10C4.1.3 | HB 11029 | 29 April 1992 |
| 9G2.1.3 | HB 11030 | 29 April 1992 |
| 9D4.9.1 | HB 11031 | 29 April 1992 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit or for the enforceable life of the patent or for a period of five years after the last request or for the effective life of the patent, whichever is longer. The organisms will be made available by ATCC under the terms of the Budapest Treaty, and subject to an agreement between Genentech, Inc. and ATCC, which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

In respect of those designations in which a European patent is sought, a sample of the deposited microorganism will be made available until the publication of the mention of the grant of the European patent or until the date on which the application has been refused or withdrawn or is deemed to be withdrawn, only by the issue of such a sample to an expert nominated by the person requesting the sample. (Rule 28(4) EPC)

Although the foregoing refers to particular preferred embodiments, it will be understood that the present invention is not so limited. It will occur to those ordinarily skilled in the art that various modifications may be made to the disclosed embodiments without diverting from the overall concept of the invention. All such modifications are intended to be within the scope of the invention.

What is claimed is:

1. An isolated nucleic acid encoding an anti-αvβ3 monoclonal antibody that binds to the same αvβ3 epitope that is bound by an antibody selected from the group consisting of 10C4.1.3 produced by the hybridoma cell line deposited with the ATCC as designation HB 11029, 9G2.1.3 produced by the hybridoma cell line deposited with the ATCC as designation HB 11030 and 9D4.9.1 produced by the hybridoma cell line deposited with the ATCC as designation HB 11031.

2. The isolated nucleic acid of claim 1, wherein said anti-αvβ3 monoclonal antibody (1) binds to osteoclasts and (2) inhibits the binding of αvβ3-expressing cells to fibrinogen.

3. The isolated nucleic acid of claim 1, wherein said anti-αvβ3 monoclonal antibody inhibits the binding of αvβ3-expressing cells to vitronectin.

4. The isolated nucleic acid of claim 1, wherein said anti-αvβ3 monoclonal antibody recognizes the αvβ3 complex.

5. The isolated nucleic acid of claim 1, wherein said anti-αvβ3 monoclonal antibody binds to the same αvβ3 epitope as does the antibody 10C4.1.3 produced by the hybridoma cell line deposited with the ATCC as designation HB 11029.

6. The isolated nucleic acid of claim 1, wherein said anti-αvβ3 monoclonal antibody binds to the same αvβ3 epitope as does the antibody 9G2.1.3 produced by the hybridoma cell line deposited with the ATCC as designation HB 11030.

7. The isolated nucleic acid of claim 1, wherein said anti-αvβ3 monoclonal antibody binds to the same αvβ3 epitope as does the antibody 9D4.9.1 produced by the hybridoma cell line deposited with the ATCC as designation HB 11031.

8. The isolated nucleic acid of claim 7, wherein said anti-αvβ3 monoclonal antibody has an affinity for αvβ3 that is equal to or higher than that of antibody 9D4.9.1 produced by the hybridoma cell line deposited with the ATCC as designation HB 11029.

9. The isolated nucleic acid of claim 1, wherein said anti-αvβ3 monoclonal antibody recognizes the β3 portion of the αvβ3 molecule.

10. The isolated nucleic acid of claim 1, wherein said anti-αvβ3 monoclonal antibody is incapable of binding to IIbIIIa.

11. The isolated nucleic acid of claim 1, wherein said anti-αvβ3 monoclonal antibody binds to αvβ3 on osteoclasts but is incapable of binding to αvβ3 on human umbilical vein endothelium.

12. The isolated nucleic acid of claim 1, wherein said anti-αvβ3 monoclonal antibody comprises an Fc domain having an immunoglobulin effector function.

13. The isolated nucleic acid of claim 1, wherein said anti-αvβ3 monoclonal antibody is monovalent.

14. The isolated nucleic acid of claim 1, wherein said anti-αvβ3 monoclonal antibody comprises an Fc domain of IgA, IgD, IgE, IgG or IgM.

15. An isolated nucleic acid encoding a first anti-αvβ3 monoclonal antibody, wherein the binding of said antibody to its target epitope is inhibited by a second monoclonal antibody selected from the group consisting of 10C4.1.3 produced by the hybridoma cell line deposited with the ATCC as designation HB 11029, 9G2.1.3 produced by the hybridoma cell line deposited with the ATCC as designation HB 1100 and 9D4.9.1 produced by the hybridoma cell line deposited with the ATCC as designation HB 11031.

16. The isolated nucleic acid of claim 15, wherein said anti-αvβ3 monoclonal antibody (1) binds to osteoclasts and (2) inhibits the binding of αvβ3-expressing cells to fibrinogen.

17. The isolated nucleic acid of claim 15, wherein said anti-αvβ3 monoclonal antibody inhibits the binding of αvβ3-expressing cells to vitronectin.

18. The isolated nucleic acid of claim 15, wherein said anti-αvβ3 monoclonal antibody recognizes the αvβ3 complex.

19. The isolated nucleic acid of claim 15, wherein said anti-αvβ3 monoclonal antibody binds to the same αvβ3 epitope as does the antibody 10C4.1.3 produced by the hybridoma cell line deposited with the ATCC as designation HB 11029.

20. The isolated nucleic acid of claim 15, wherein said anti-αvβ3 monoclonal antibody binds to the same αvβ3 epitope as does the antibody 9G2.1.3 produced by the hybridoma cell line deposited with the ATCC as designation HB 11030.

21. The isolated nucleic acid of claim 15, wherein said anti-αvβ3 monoclonal antibody binds to the same αvβ3 epitope as does the antibody 9D4.9.1 produced by the hybridoma cell line deposited with the ATCC as designation HB 11031.

22. The isolated nucleic acid of claim 15, wherein said anti-αvβ3 monoclonal antibody has an affinity for αvβ3 that is equal to or higher than that of antibody 9D4.9.1 produced by the hybridoma cell line deposited with the ATCC as designation HB 11029.

23. The isolated nucleic acid of claim 15, wherein said anti-αvβ3 monoclonal antibody recognizes the β3 portion of the αvβ3 molecule.

24. The isolated nucleic acid of claim 15, wherein said anti-αvβ3 monoclonal antibody is incapable of binding to IIbIIIa.

25. The isolated nucleic acid of claim 15, wherein said anti-αvβ3 monoclonal antibody binds to αvβ3 on osteoclasts but is incapable of binding to αvβ3 on human umbilical vein endothelium.

26. The isolated nucleic acid of claim 15, wherein said anti-αvβ3 monoclonal antibody comprises an Fc domain having an immunoglobulin effector function.

27. The isolated nucleic acid of claim 15, wherein said anti-αvβ3 monoclonal antibody is monovalent.

28. The isolated nucleic acid of claim 15, wherein said anti-αvβ3 monoclonal antibody comprises an Fc domain of IgA, IgD, IgE, IgG or IgM.

\* \* \* \* \*